United States Patent
Ho et al.

(10) Patent No.: US 9,981,233 B2
(45) Date of Patent: May 29, 2018

(54) PORTABLE MIXER AND DISPENSER FOR MULTI-COMPONENT SUBSTANCES

(71) Applicant: Phillip Phung-I Ho, Santa Barbara, CA (US)

(72) Inventors: Phillip Phung-I Ho, Santa Barbara, CA (US); Chieh-Yu Cheng, New Taipei (TW); Chu-Chen Wang, New Taipei (TW); Chung-Chieh Lee, New Taipei (TW)

(73) Assignee: Phillip Phung-I HO, Santa Barbara, CA (US)

( * ) Notice: Subject to any disclaimer, the term of this patent is extended or adjusted under 35 U.S.C. 154(b) by 370 days.

(21) Appl. No.: 14/808,836

(22) Filed: Jul. 24, 2015

(65) Prior Publication Data

US 2017/0021316 A1    Jan. 26, 2017

(51) Int. Cl.
| | |
|---|---|
| *B01F 13/00* | (2006.01) |
| *B01F 15/00* | (2006.01) |
| *A61C 5/64* | (2017.01) |
| *A61C 5/68* | (2017.01) |
| *B01F 15/02* | (2006.01) |

(52) U.S. Cl.
CPC ............ *B01F 13/0027* (2013.01); *A61C 5/64* (2017.02); *A61C 5/68* (2017.02); *B01F 15/00538* (2013.01); *B01F 15/0226* (2013.01); *B01F 15/0237* (2013.01); *B01F 2215/0039* (2013.01)

(58) Field of Classification Search
CPC .............. B01F 13/0027; B01F 15/0237; B01F 15/0226; B01F 15/00538; B01F 2215/0039; A61C 5/68; A61C 5/64

USPC ......... 366/171.1, 172.1–173.2, 176.1, 181.5, 366/189; 222/325–327, 145.5–145.6
See application file for complete search history.

(56) References Cited

U.S. PATENT DOCUMENTS

| | | | |
|---|---|---|---|
| 4,164,021 A | 8/1979 | Nishitani et al. | |
| 4,171,072 A | 10/1979 | Davis, Jr. | |
| 4,249,677 A | 2/1981 | Davis, Jr. | |
| 4,322,022 A * | 3/1982 | Bergman ............ | B05C 17/0103 222/327 |
| 4,615,469 A * | 10/1986 | Kishi ................... | B05C 17/0103 222/327 |
| 5,058,781 A | 10/1991 | Aronie et al. | |
| 5,286,105 A | 2/1994 | Herold et al. | |
| 6,089,407 A * | 7/2000 | Gardos ............... | B05C 17/0103 222/1 |

(Continued)

FOREIGN PATENT DOCUMENTS

EP          0057465 A2 *  8/1982

*Primary Examiner* — Charles Cooley
(74) *Attorney, Agent, or Firm* — Kolisch Hartwell, P.C.

(57) ABSTRACT

A portable mixer for medication and/or dental impression material includes a gear assembly and an upper lid. The gear assembly comprises a helical gear with a bidirectional bearing, a clutch shell with a unidirectional bearing meshing with the helical gear, a spring positioned between the helical gear and the clutch shell, two pinions respectively positioned beside the clutch shell and the helical gear, and a shifting shaft mounted transversely through each of the two pinions, the helical gear, the bidirectional bearing, the spring, the unidirectional bearing, and the clutch shell. The upper lid comprises a fastener and a switch cover co-acted with the fastener and detachably contacting the helical gear and the clutch shell.

6 Claims, 7 Drawing Sheets

(56) References Cited

U.S. PATENT DOCUMENTS

| | | | |
|---|---|---|---|
| 6,540,113 B2 * | 4/2003 | Gardos | B05C 17/0103 222/137 |
| 7,387,432 B2 | 6/2008 | Lu et al. | |
| 8,448,825 B2 | 5/2013 | Mitrovic et al. | |
| 9,616,400 B2 * | 4/2017 | Rahm | B01F 15/0278 |
| 9,827,539 B2 * | 11/2017 | Ho | B01F 7/00141 |
| 2004/0182882 A1 * | 9/2004 | Langer | A61C 9/0026 222/145.6 |
| 2008/0144426 A1 * | 6/2008 | Janssen | B01F 7/00216 366/130 |
| 2009/0101673 A1 * | 4/2009 | Alioto | B05C 17/00553 222/113 |
| 2010/0143864 A1 * | 6/2010 | An | A61C 9/0026 433/89 |
| 2014/0036616 A1 * | 2/2014 | Ghosh | B01F 13/0027 366/129 |
| 2014/0301153 A1 * | 10/2014 | Buck | B05C 17/00566 366/130 |
| 2014/0301156 A1 * | 10/2014 | Rahm | B05C 17/00566 366/184 |
| 2014/0346190 A1 * | 11/2014 | Buck | B05C 17/0133 222/137 |
| 2014/0346251 A1 * | 11/2014 | Schultheiss | B05B 7/24 239/314 |

* cited by examiner

PORTABLE MIXER AND DISPENSER FOR MULTI-COMPONENT SUBSTANCES

FIELD OF THE INVENTION

The present invention relates to a portable mixer, especially to a portable mixer with a gear assembly for quick replacement of cartridges.

BACKGROUND AND DESCRIPTION OF THE PRIOR ART

A conventional hand-held electric caulking gun disclosed in U.S. Pat. No. 4,171,072 comprises a caulk-driving piston forced through the caulk-retaining receptacle of the gun. The gun includes a clutch for drivably disengaging the drive source from the piston and a releasing device for allowing the piston to be disengaged from its driving linkage with a motor.

A conventional quick release for helically-threaded drive unit disclosed in U.S. Pat. No. 4,322,022 is provided with a quick release feature. As the release feature is activated, the active portions of the drive nut of a lead screw in the drive train are disconnected from the lead screw, allowing the internal pressure in the chamber of the cartridge to be quickly equilibrated by pushing the piston and its lead screw backwards. Then, the dispensing can be stopped and sharply curtailed, merely by releasing the trigger on the power hand tool and activating the quick release.

A conventional apparatus for mixing and dispersing multiple-component substances disclosed in U.S. Pat. No. 5,286,105 comprises two cartridges with pistons and advanced in common by an electrical motor via a magnetic clutch. When switching off the motor and disengaging the clutch, the pistons are manually retracted and re-advanced. Then the pistons entrain a shaft which serves to drive a mixer head. The cartridge connecting with the mixer head can be removed as a unit from the apparatus and replaced by another unit for exchanging the emptied cartridges.

The conventional apparatus for mixing and delivering multi-component substances, particularly for expressing said mixed substances onto a tray during the taking of a dental impression, comprises a housing, an electronic button, driving gears mounted on the housing, two gear racks, a dual-barrel cartridge, and a mixer head. The driving gears, the two gear racks, the dual-barrel cartridge, and the mixer head are positioned in the housing. The driving gears trigger motion of the two gear racks, and the two gear racks are each respectively connected to each of the two chambers of the cartridge, pushing the two component substances contained in each of the chambers into the mixer head. As a user pushes the electronic button, each of the two gear racks will be pushed equally and in synchrony into each of the two chambers of the cartridge resulting in the different component substances contained in each of the chambers being pushed into the mixer head; in the meantime, the build-up of viscoelastic pressure inside the cartridge will cause a slight expansion of its walls. Therefore, as the user stops pushing the electronic button, the relaxation of the viscoelastic pressure will allow relaxation of the cartridge walls, resulting in an undesirable oozing and waste of the component substances.

Besides, as the cartridge is emptied and the user wants to replace it with a full one, due to the manner by which the pistons and gears are positioned in the cartridge, the user has to press and hold a reverse button in order to allow the gears to rotate in reverse, which causes the pistons to disengage from the cartridge. Thus, it is rather time consuming to change the cartridge.

Furthermore, the desktop conventional apparatus for mixing different component substances of the silicone-based dental impression material is heavy and not easy to move. Therefore, being non-portable, each treatment room is required to have its own heavy, bulky, and expensive machine.

SUMMARY OF THE INVENTION

To overcome the shortcomings, the present invention provides a hand-held, light, and portable apparatus for mixing and expressing the mixed materials with a gear assembly which mitigates or obviates the aforementioned problems.

The portable mixer in accordance with the present invention has a main body, at least two gear racks, a gear assembly, an upper lid and a worm-geared motor. The main body is comprised of a dual-barrel cartridge and a periphery connected to the dual-barrel cartridge. At the base of the dual-barrel cartridge, in the middle of one of its four sides, a rectangular groove is formed to allow firm seating of the dual-barrel cartridge into the housing receptacle.

Each of the at least two gear racks respectively contacts the rear bottom of each of the two chambers of the dual-barrel cartridge on one end and connects with the driving gears on the other end.

The gear assembly comprises a helical gear, a bidirectional bearing mounted into the helical gear, a clutch shell meshing with the helical gear, a unidirectional bearing mounted into the clutch shell, a spring positioned between the helical gear and the clutch shell, at least two pinions respectively positioned beside the clutch shell opposite to the helical gear, and a shifting shaft transversely mounted through each of the at least two pinions, the helical gear, the bidirectional bearing, the unidirectional bearing, the clutch shell, and the spring. The helical gear comprises multiple ratchet teeth disposed annularly. The clutch shell comprises multiple pawls disposed annularly and meshes with the ratchet teeth.

The upper lid covers the main body and comprises a fastener mounted on the upper lid and a switch cover co-acting with the fastener. The fastener also comprises a fastening part which can be locked onto the groove of the dual-barrel cartridge. The switch cover detachably contacts the helical gear opposite to the annularly disposed ratchet teeth as well as the clutch shell opposite to the multiple annularly disposed pawls.

The worm-geared motor comprises a worm-gear meshing with the helical gear of the gear assembly.

Preferably, the upper lid further comprises a sliding groove next to the fastener of the upper lid and a sliding element mounted in the sliding groove.

Preferably, the portable mixer in accordance with the present invention further comprises a connector mounted on each of the at least two gear racks opposite to the teeth of the gear rack, and the connector comprises a protrusion connected to the sliding element of the upper lid.

Preferably, the portable mixer in accordance with the present invention further comprises a mixer head connecting to and communicating with each barrel of the dual-barrel cartridge opposite to the rear bottom.

More preferably, the portable mixer in accordance with the present invention further comprises a housing being open and accommodating the dual-barrel cartridge, the main body and the worm geared motor.

In a preferred embodiment, an amount of the at least two pinions is two and an amount of the at least two gear racks is two.

The portable mixer provided by the present invention prevents the component substances from overflowing from the mixer head upon stopping of the gear assembly. Besides, the portable mixer provided by the present invention is time-efficient for users to change or replace the cartridges quickly.

DETAILED DESCRIPTION OF THE PREFERRED EMBODIMENTS

Figure 1:
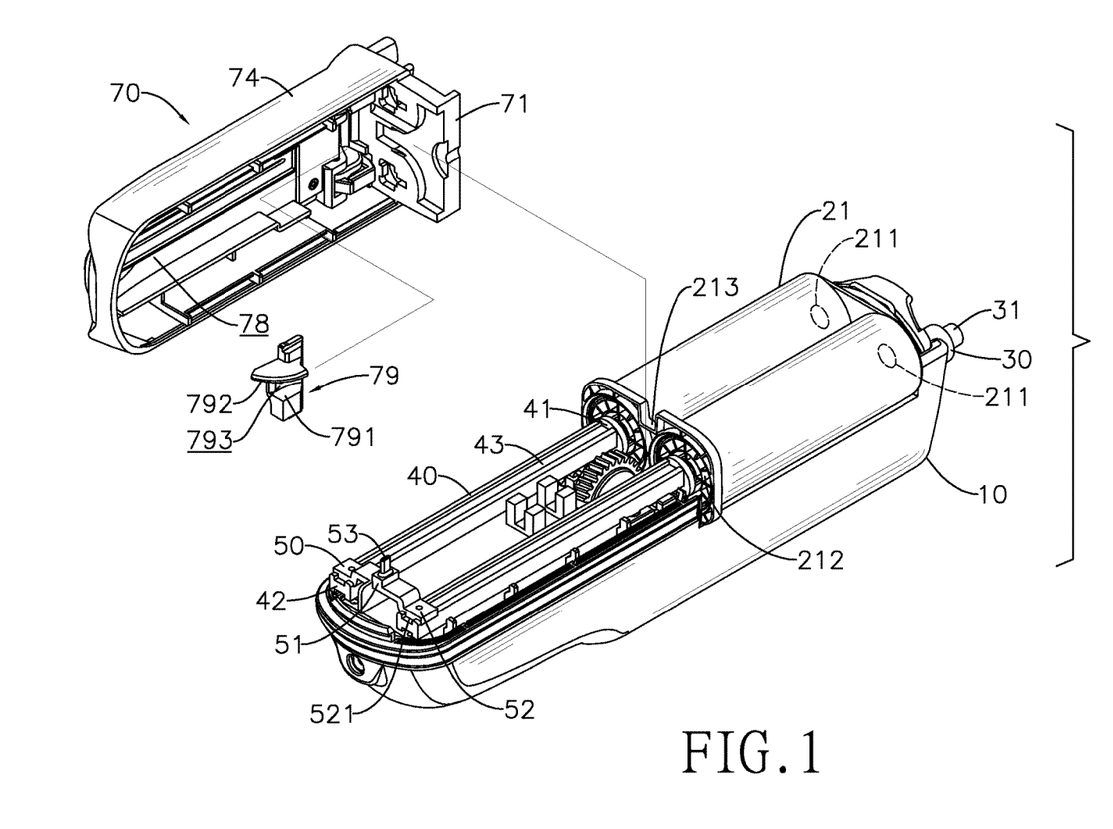
FIG. 1 is an exploded perspective view of a portable mixer in accordance with the present invention.
Figure 2:
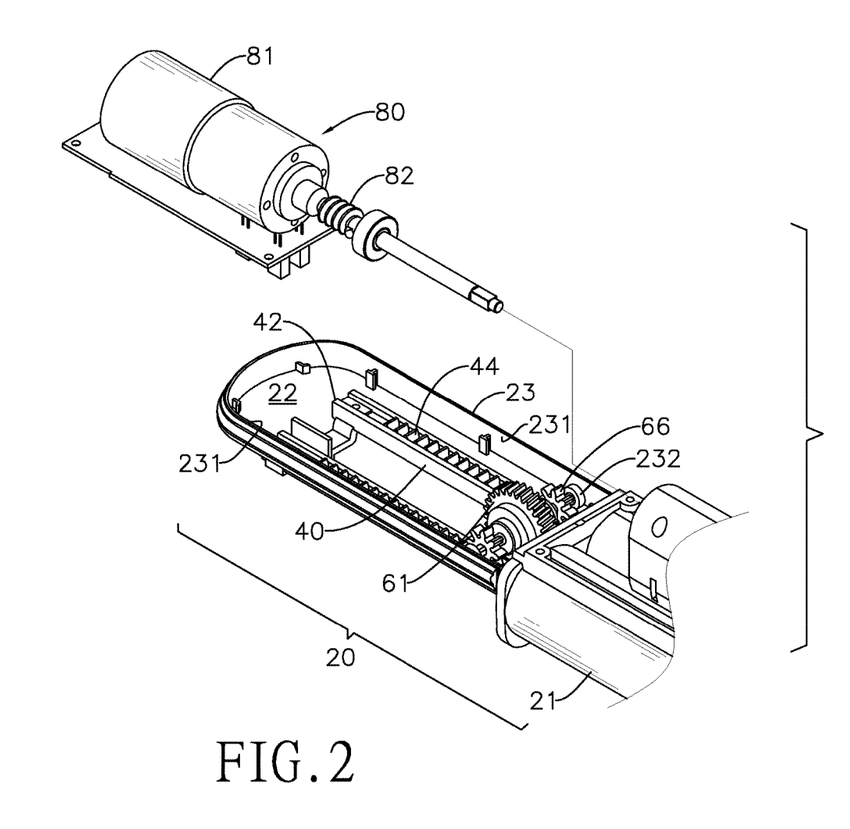
FIG. 2 is an exploded bottom view of a main body, a gear assembly and a worm-geared motor in FIG. 1.
Figure 3:
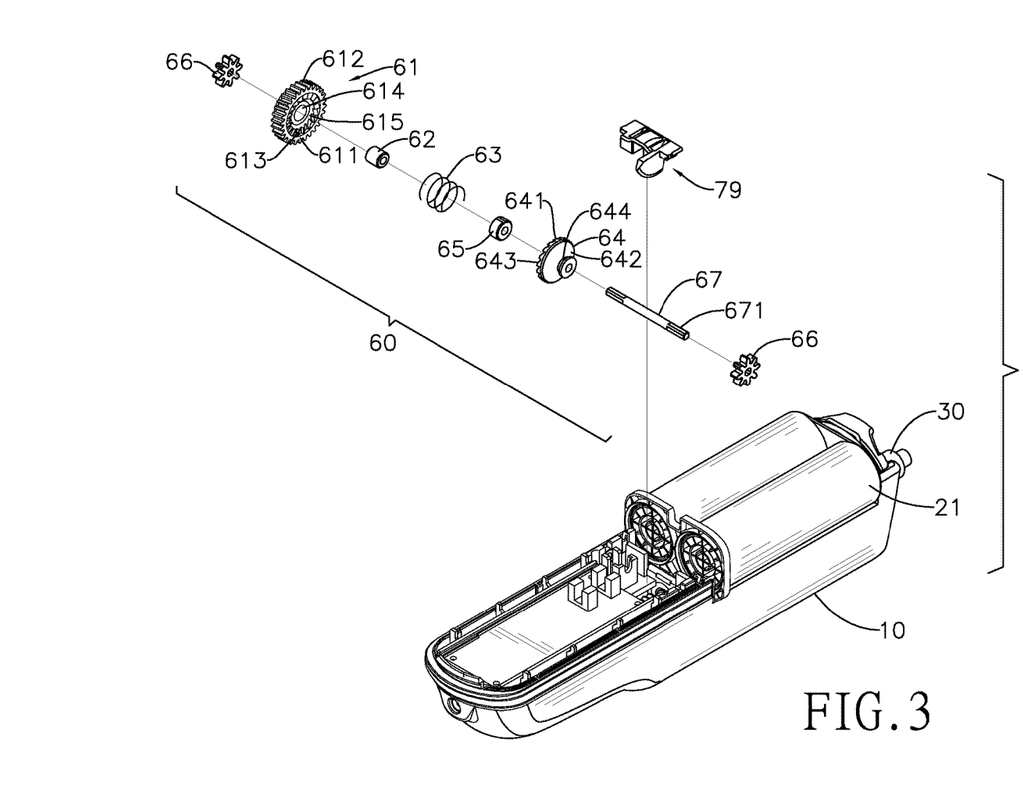
FIG. 3 is an exploded view of a housing and the gear assembly in FIG. 1.

With references to FIG. 1, FIG. 2 and FIG. 3, a portable mixer in accordance with the present invention comprises a housing 10, a main body 20, a mixer head 30, at least two gear racks 40, a connector 50, a gear assembly 60, an upper lid 70, and a worm geared motor 80.

With references to FIG. 1, the housing 10 is open and comprises a front receiving space and a back receiving space communicating with the front receiving space.

With references to FIG. 1 and FIG. 2, the main body 20 comprises a dual-barrel cartridge 21, a receiving space 22 and a periphery 23, wherein the dual-barrel cartridge 21 is connected with the periphery 23, and the receiving space 22 is disposed between the dual-barrel cartridge 21 and the periphery 23. The first embodiment of the present invention comprises the dual-barrel cartridge 21. Each chamber of the dual-barrel cartridge 21 is cylindrical and is positioned in parallel with the front receiving space of the housing 10. Each chamber of the dual-barrel cartridge 21 comprises a front opening 211 and a rear bottom 212 opposite to the front opening 211, and the two chambers of the dual-barrel cartridge 21 are loaded with different component substances. A rectangular groove 213 is formed between two barrels of the dual-barrel cartridges 21 at the rear bottom 212.

The receiving space 22 is enclosed by the periphery 23 and the dual-barrel cartridges 21, and the receiving space 22 is adjacent to the rear bottom 212 of each of the barrel of the dual-barrel cartridge 21. The periphery 23 is connected to the rear bottom 212 of the dual-barrel cartridge 21 and positioned in the back receiving space of the housing 10, and the periphery 23 comprises two opposite walls 231, two fixed portions 232, and a rim opposite to the housing 10. Each of the two fixed portions 232 comprises a recess and the two fixed portions 232 are each respectively mounted on the opposite walls 231 close to each of the rear bottoms 212 of the dual-barrel cartridge 21.

With reference to FIG. 1, the mixer head 30 connects to and communicates with the front opening 211 of each of the two chambers of the dual-barrel cartridge 21. The mixer head 30 comprises an exit 31.

With references to FIG. 1 and FIG. 2, the first embodiment of the present invention comprises two gear racks 40. The two gear racks 40 are rectangular and positioned in the back receiving space of the housing 10, and each of the two gear racks 40 comprises a front end 41 and a back end 42 opposite to the front end 41, a surface 43, a bottom opposite to the surface 43, and multiple teeth 44. The surface 43 is positioned between the front end 41 and the back end 42. The multiple teeth 44 are mounted on the bottom of each of the two gear racks 40.

With references to FIG. 1 and FIG. 2, the connector 50 comprises a central portion 51, two ends 52, and a protrusion 53. The central portion 51 is positioned between the two ends 52, and the protrusion 53 is mounted on the central portion 51. Each of the two ends 52 comprises an abutment 521 respectively abutted against the surface 43 of each of the two gear racks 40 at the back end 42 thereof.

With reference to FIG. 2 and FIG. 3, the gear assembly 60 comprises a helical gear 61, a bidirectional bearing 62, a spring 63, a clutch shell 64, a unidirectional bearing 65, at least two pinions 66, and a shifting shaft 67. The helical gear 61 comprises a first side surface 611, a second side surface 612 opposite to the first side surface 611, multiple ratchet teeth disposed annularly 613, a mounting hole 614, and an annular recess 615. The annularly disposed ratchet teeth 613 are formed on the first side surface 611. The mounting hole 614 is disposed in the center of the helical gear 61 and through the first side surface 611 and the second side surface 612. The annular recess 615 is formed between the ratchet teeth 613 and the mounting hole 614.

The bidirectional bearing 62 is mounted into the mounting hole 614 of the helical gear 61.

The spring 63 comprises two ends, wherein one of the ends of the spring 63 is positioned in the annual recess 615 of the helical gear 61 and the spring 63 is mounted around the bidirectional bearing 62.

The clutch shell 64 comprises a first side surface 641, a second side surface 642 opposite to the first side surface 641, multiple pawls disposed annularly 643, and a mounting hole 644. The second side surface 642 contacts the other end of the spring 63 opposite to the annual recess 615 of the helical gear 61. The annularly disposed multiple pawls 643 are formed on the first side surface 641 and are meshing with the ratchet teeth 613 of the helical gear 61. The mounting hole 644 is disposed in the center of the clutch shell 64 and through the first side surface 641 and the second side surface 642.

The unidirectional bearing 65 is mounted into the mounting hole 644 of the clutch shell 64.

The first embodiment of the present invention comprises two pinions 66. Each of the pinions 66 has multiple teeth. One of the two pinions 66 is positioned beside the second side surface 642 of the clutch shell 64 and the other of the two pinions 66 is positioned beside the second side surface 612 of the helical gear 61. Each of the teeth of the two pinions 66 respectively engages each of the multiple teeth 44 of the two gear racks 40.

The shifting shaft 67 comprises two terminals 671, and the shifting shaft 67 is mounted transversely through each of the pinions 66, the helical gear 61, the bidirectional bearing 62, the spring 63, the clutch shell 64, and the unidirectional bearing 65. Each of the two terminals 671 of the shifting shaft 67 is respectively inserted into each of the recesses of the two fixed portions 232, allowing the gear assembly 60 to be connected to the main body 20.

Figure 4:
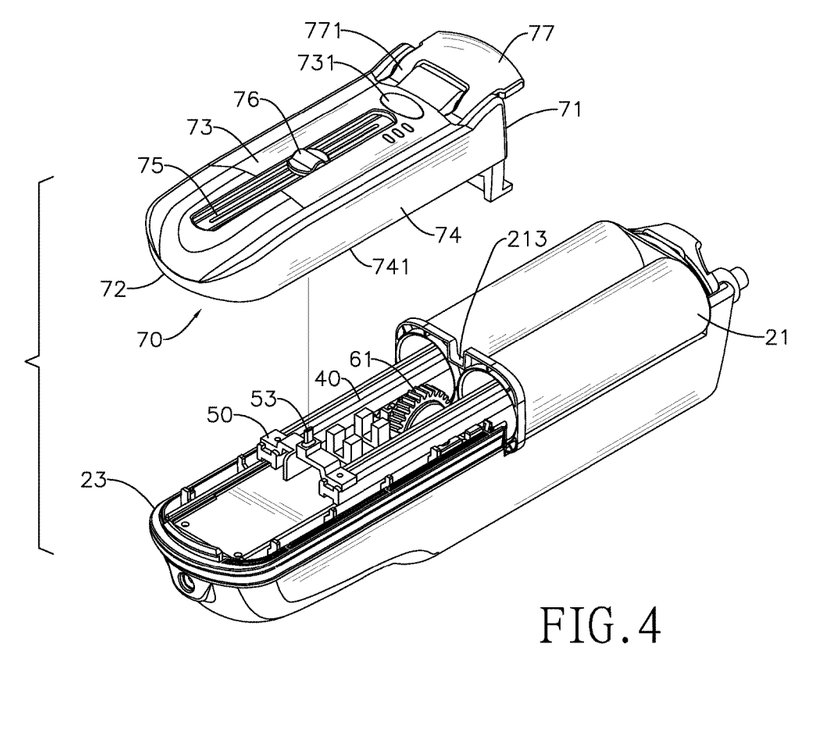
FIG. 4 is an exploded view of an upper lid and the housing in FIG. 1.

With references FIG. 1, FIG. 2 and FIG. 4, the upper lid 70 comprises a front end 71, a back end 72 opposite to the front end 71, a roof 73, a peripheral side 74, a sliding groove 75, a sliding element 76, a fastener 77, a receiving space 78, and a switch cover 79.

The roof 73 is positioned between the front end 71 and the back end 72, and the roof 73 comprises an electronic button 731. The electronic button 731 is mounted at the front end 71 of the roof 73.

With references to FIG. 1, FIG. 3, FIG. 4 and FIG. 5, the peripheral side 74 is connected to the roof 73, and the peripheral side 74 comprises a rim 741 opposite to the roof 73. The rim 741 is detachably connected to the rim of the periphery 23 of the main body 20, allowing the upper lid 70 to cover the periphery 23 of the main body 20 as well as the back receiving space of the housing 10.

The sliding groove 75 is disposed in the center of the roof 73 extending from the front end 71 to the back end 72 of the upper lid 70.

The sliding element 76 is mounted in the sliding groove 75, and the sliding element 76 is connected to the protrusion 53 of the connector 50 through the sliding groove 75, allowing the two gear racks 40 to be slid by shifting the sliding element 76. As such, each of the two gear racks 40 can be pulled out of the rear bottom 212 of each of the two chambers of the dual-barrel cartridge 21, facilitating quick change or replacement of the dual-barrel cartridge 21.

The fastener 77 comprises two mounting ends 771 and a fastening part 772. The mounting end 77 is mounted at the front end 71 of the upper lid 70, allowing the fastener 77 to be rotated close to or away from the rim 741 of the peripheral side 74. The fastening part 772 is connected to the fastener 77 opposite to the two mounting ends 771 and the fastening part 772 can be securely seated onto the groove 213 between the two chambers of the dual-barrel cartridge 21 thus allowing for the secured lock-down of the dual-barrel cartridge 21 with the up lid 70. As the fastener 77 is rotated close to the rim 741 of the peripheral side 74, the fastener 77 will lock down the dual-barrel cartridge 21 in the front receiving space of the housing 10. On the contrary, as the fastener 77 is rotated away from the rim 741 of the peripheral side 74, the fastener 77 will unlock the dual-barrel cartridge 21 from the front receiving space of the housing 10.

The receiving space 78 is formed between the roof 73 and the peripheral side 74.

The switch cover 79 comprises a first side surface 791, a second side surface 792 opposite to the first side surface 791, and a channel 793 formed between the first side surface 791 and the second side surface 792. The switch cover 79 is mounted in the receiving space 78 and is co-acted with the fastener 77. The first side surface 791 detachably contacts the second side surface 642 of the clutch shell 64, and the second side surface 792 detachably contacts the second side surface 612 of the helical gear 61.

With references to FIGS. 1, 3-4, and 6, as the fastener 77 locks down the dual-barrel cartridge 21 to the front receiving space of the housing 10, the first side surface 791 and the second side surface 792 of the switch cover 79 respectively contact the second side surface 642 of the clutch shell 64 and the second side surface 612 of the helical gear 61. The spring 63 positioned between the helical gear 61 and the clutch shell 64 is compressed, and the annularly disposed ratchet teeth 613 of the helical gear 61 are meshed with the annularly disposed multiple pawls 643 of the clutch shell 64.

As such, the helical gear 61 and the shifting shaft 67 are restricted to be rotated in one way direction by combining with the clutch shell 64 mounted with the unidirectional bearing 65, allowing each of the two gear racks 40 to be moved toward each of the chambers of the dual-barrel cartridges 21 rather than rotating reversely. Besides, the combination of the ratchet teeth 613 and the multiple pawls 643 also prevent the helical gear 61 from rotating in the opposite direction.

Figure 7:
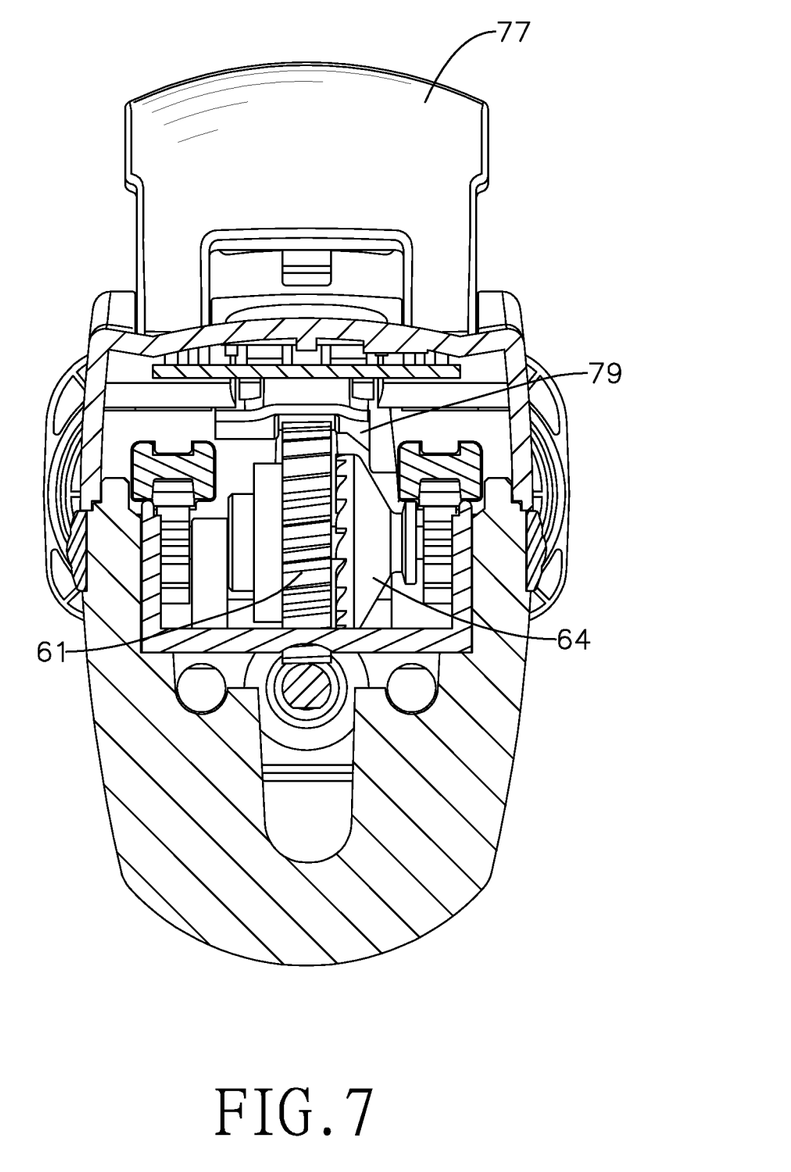
FIG. 7 is another cross-sectional view of the gear assembly in FIG. 3.

With reference to FIGS. 3-4 and 7, as the fastener 77 unlocks the dual-barrel cartridges 21 from the front receiving space of the housing 10, the switch cover 79 detaches from the helical gear 61 and the clutch shell 64. In the meanwhile, the spring 63 is released, allowing the helical gear 61 and the clutch shell 64 to be separated. As such, the helical gear 61 can be rotated either clockwise or counterclockwise.

With reference to FIGS. 1 and 2, the worm-geared motor 80 comprises a motor 81 and a worm gear 82. The motor 81 is positioned in the back receiving space of the housing 10. The worm gear 82 is linked with and driven by the motor 81. The worm gear 82 is meshed with the helical gear 61.

Figure 5:
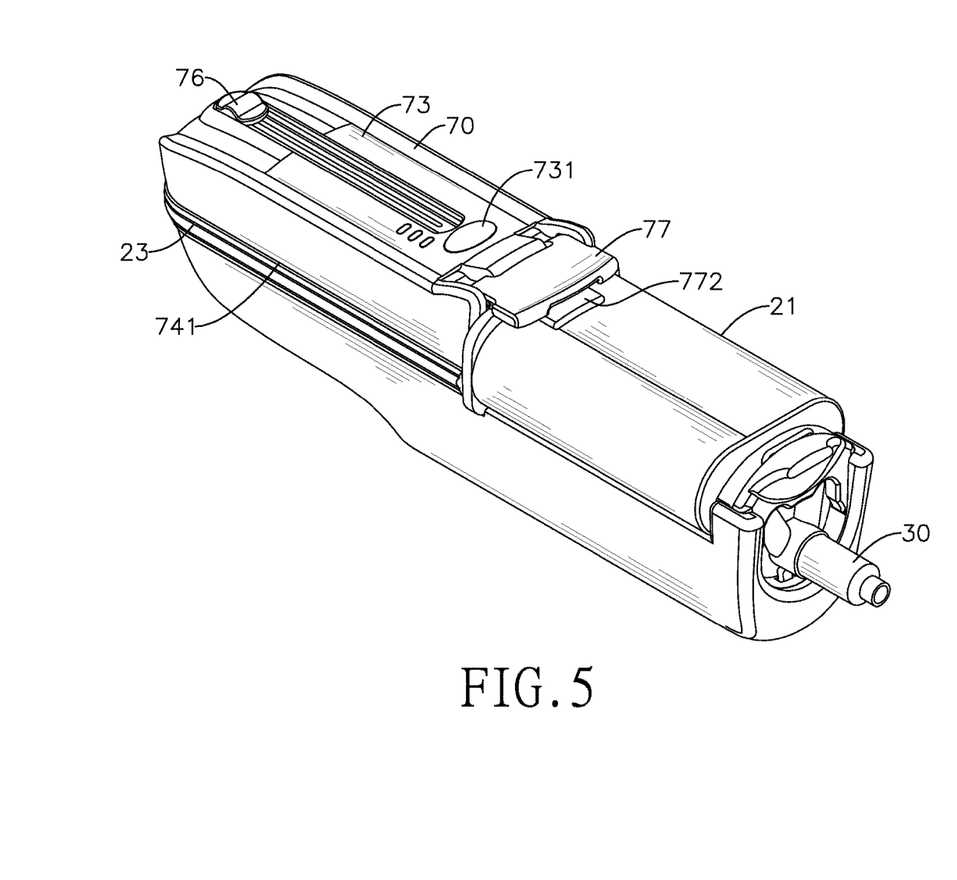
FIG. 5 is a perspective view of the portable mixer in FIG. 1.
Figure 6:
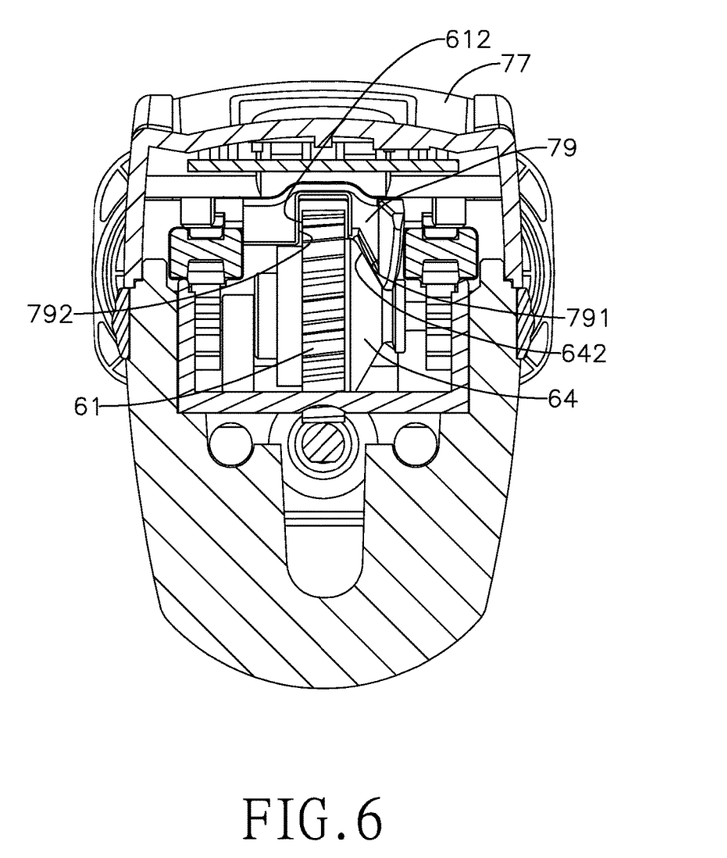
FIG. 6 is a cross-sectional view of the gear assembly in FIG. 3.

With references to FIGS. 2 and 4-5, as the portable mixer is in use, a user can push the electronic button 731, allowing the worm gear 82 to be driven by the motor 81 followed by rotating the helical gear 61 and the pinion 66, resulting in each of the two gear racks 40 being moved towards the rear end of each of the chambers of the dual-barrel cartridges 21, thus pushing the component substances into the mixer head 30; in the meanwhile, an inner pressure rises in each of the chambers of the dual-barrel cartridges 21. As the user stops pushing the electronic button 731, each of the two gear racks 40 will not only stop moving toward each of the chambers of the dual-barrel cartridge 21, it will also be moved slightly back in the opposite direction, thus allowing for dissipation of the built-up viscoelastic pressure in the posterior direction. Therefore, the present invention prevents the component substances from overflowing from the mixer head 30 upon release of the electronic button 731. Besides, if the component substances loaded in the dual-barrel cartridge 21 runs out and the user wants to quickly change to a new one, the user can unlock the upper lid 70 by the fastener 77. Then, the user can manually slide the sliding element 76 away from the dual-barrel cartridge 21, allowing the two gear racks 40 to be pulled quickly out of the chambers of the dual-barrel cartridge 21. The main advantage of this design is the quick speed with which the user can change or replace the emptied dual-barrel cartridge 21 instead of the time-consuming process of resetting the reverse parameter of a machine for rotating the helical gear 61 in an opposite direction. Therefore, the present invention is also time efficient. Furthermore, the quick speed of changing cartridges is critical because of the fast setting times of the mixed component substances involved in taking dental impressions.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A portable mixer for mixing and dispensing multi-component substances comprising:

a main body having:
- a dual-barrel cartridge having two barrels, wherein each barrel of the dual-barrel cartridge comprising
- a rear bottom; and
- a groove formed between the rear bottoms of the barrels;
- a periphery connected to the rear bottom of the dual-barrel cartridge and comprising:
- two opposite walls; and
- two fixed portions, wherein the two fixed portions are each respectively mounted on the two opposite walls, and each of the two fixed portions respectively comprises a recess;
- at least two gear racks, wherein one end of each of the at least two gear racks contacts the rear bottom of each barrel of the dual-barrel cartridge, wherein each of the at least two gear racks comprises
- multiple teeth mounted on the at least two gear racks;
- a gear assembly comprising
- a helical gear comprising
- multiple ratchet teeth disposed annularly,
- a mounting hole disposed in a center of the helical gear and through the helical gear; and
- an annular recess formed between the ratchet teeth and the mounting hole;
- a bidirectional bearing mounted into the mounting hole of the helical gear,
- a clutch shell comprising
- multiple pawls disposed annularly and meshing with the ratchet teeth of the helical gear; and
- a mounting hole disposed in a center of the clutch shell and through the clutch shell;
- a unidirectional bearing mounted into the mounting hole of the clutch shell,
- a spring comprising two ends, wherein one of the ends of the spring is positioned in the annual recess of the helical gear, and the other end of the spring contacts the clutch shell;
- at least two pinions, wherein one of the at least two pinions is positioned beside the clutch shell opposite to the helical gear, and the other of the at least two pinions is positioned beside the helical gear opposite to the clutch shell; wherein each of the at least two pinions has teeth engaged with each of the at least two gear racks; and
- a shifting shaft comprising two terminals and mounted transversely through each of the at least two pinions, the helical gear, the bidirectional bearing, the clutch shell, the spring, and the unidirectional bearing; wherein each of the terminals is respectively inserted into each of the two fixed portions of the main body;
- an upper lid covering the main body and comprising
- a fastener mounted on the upper lid and comprising
- a fastening part locked onto the groove of the dual-barrel cartridge; and
- a switch cover co-acted with the fastener, wherein the switch cover detachably contacts the helical gear opposite to the ratchet teeth and the clutch shell opposite to the pawls;
- a worm-geared motor comprising
- a worm gear meshing with the helical gear of the gear assembly; and
- a mixer head connecting to and communicating with each of the barrels of the dual-barrel cartridge and being opposite to the rear bottom.

2. The portable mixer as claimed in claim 1, wherein the upper lid further comprises
- a sliding groove next to the fastener of the upper lid; and
- a sliding element mounted in the sliding groove.

3. The portable mixer as claimed in claim 2, wherein the portable mixer further comprises
- a connector mounted on each of the at least two gear racks opposite to the teeth of the gear rack and comprising
- a protrusion connected to the sliding element of the upper lid.

4. The portable mixer as claimed in claim 1, wherein the portable mixer further comprises a housing being open; wherein the housing accommodates the dual-barrel cartridge, the main body and the worm geared motor.

5. The portable mixer as claimed in claim 1, wherein an amount of the at least two pinions is two.

6. The portable mixer as claimed in claim 5, wherein an amount of the at least two gear racks is two.

* * * * *